(12) United States Patent
Lin

(10) Patent No.: US 7,960,461 B2
(45) Date of Patent: Jun. 14, 2011

(54) NATURAL OIL GELS AND THEIR APPLICATION

(76) Inventor: Samuel Q. Lin, Newark, NJ (US)

( * ) Notice: Subject to any disclaimer, the term of this patent is extended or adjusted under 35 U.S.C. 154(b) by 0 days.

(21) Appl. No.: 12/589,358

(22) Filed: Oct. 21, 2009

(65) Prior Publication Data

US 2010/0041754 A1 Feb. 18, 2010

Related U.S. Application Data

(63) Continuation of application No. 11/973,826, filed on Oct. 9, 2007, now Pat. No. 7,674,848.

(60) Provisional application No. 60/850,586, filed on Oct. 10, 2006, provisional application No. 60/900,512, filed on Feb. 9, 2007, provisional application No. 60/900,518, filed on Feb. 9, 2007.

(51) Int. Cl.
*C08K 5/101* (2006.01)
*A01N 37/00* (2006.01)

(52) U.S. Cl. .................................. 524/318; 514/558

(58) Field of Classification Search .................. 524/318
See application file for complete search history.

(56) References Cited

U.S. PATENT DOCUMENTS

| | | | |
|---|---|---|---|
| 2,798,053 A | | 7/1957 | Bown |
| 4,369,284 A | | 1/1983 | Chen |
| 4,509,949 A | | 4/1985 | Huang et al. |
| 5,221,534 A | * | 6/1993 | DesLauriers et al. ...... 424/78.03 |
| 5,496,488 A | | 3/1996 | Kacher et al. |
| 5,496,493 A | | 3/1996 | Cox et al. |
| 5,578,089 A | * | 11/1996 | Elsamaloty ................ 44/275 |
| 5,871,765 A | * | 2/1999 | Johnson et al. ............ 424/409 |
| 5,879,694 A | | 3/1999 | Morrison et al. |
| 5,952,286 A | | 9/1999 | Puvvada et al. |
| 6,066,613 A | | 5/2000 | Tsaur et al. |
| 6,067,816 A | | 5/2000 | Hodosh |
| 6,190,678 B1 | | 2/2001 | Hasenoehrl et al. |
| 6,270,836 B1 | | 8/2001 | Holman |
| 6,340,467 B1 | * | 1/2002 | Morrison .................. 424/405 |
| 6,395,690 B1 | | 5/2002 | Tsaur |
| 6,420,333 B1 | * | 7/2002 | Hsu et al. .................. 510/441 |
| 6,426,326 B1 | | 7/2002 | Mitra et al. |
| 6,440,913 B1 | | 8/2002 | Shafer et al. |
| 6,716,440 B2 | | 4/2004 | Aronson et al. |
| 6,737,394 B2 | | 5/2004 | Shana'a et al. |
| 6,923,975 B2 | | 8/2005 | Aronson et al. |
| 7,119,057 B2 | | 10/2006 | Popplewell et al. |
| 7,122,512 B2 | | 10/2006 | Brain et al. |
| 7,196,049 B2 | | 3/2007 | Brain et al. |
| 7,238,655 B2 | | 7/2007 | Ness |
| 2006/0079417 A1 | * | 4/2006 | Wagner et al. .............. 510/130 |
| 2006/0079418 A1 | | 4/2006 | Wagner et al. |
| 2006/0079420 A1 | | 4/2006 | Wagner et al. |
| 2006/0079421 A1 | | 4/2006 | Wagner et al. |
| 2006/0079422 A1 | | 4/2006 | Midha et al. |

OTHER PUBLICATIONS

IB Patentability Report, Apr. 23, 2009, Applechem Inc. et al.
Int'l Search Report, Mar. 13, 2008, Applechem Inc. et al.
ISA Written Opinion, Mar. 13, 2008, Applechem Inc. et al.

* cited by examiner

*Primary Examiner* — Ling-Siu Choi
*Assistant Examiner* — Hui Chin
(74) *Attorney, Agent, or Firm* — Gearhart Law LLC

(57) ABSTRACT

The invention is an article of manufacture, comprising a blend of: (A) from 1 to 50 weight percent of at least one block copolymer, wherein the block copolymer has at least one polystyrene block and at least one unsaturated rubber segment; and (B) from 99 to 50 weight percent of a natural oil. The natural oil of this invention is of natural animal, plant or vegetable oils or mixtures thereof, and the block copolymers have a polystyrene block and a rubber block where the rubber blocks are unsaturated rubbers such as polyisoprene, polybutadiene, or mixtures thereof. The block copolymers useful for the present invention are triblock polymers, radial (star) polymers, multiblock polymers, diblock polymers, or mixtures thereof.

22 Claims, No Drawings

NATURAL OIL GELS AND THEIR APPLICATION

CLAIM OF PRIORITY

This application is a continuation application of U.S. Ser. No. 11/973,826 filed Oct. 9, 2007, now U.S. Pat. No. 7,674,848 which claims the benefit of previously filed U.S. provisional applications 60/850,586 filed Oct. 10, 2006 entitled NOVEL CLEAR NATURAL OIL GELS; 60/900,512 filed Feb. 9, 2007 entitled PERSONAL CARE COMPOSITIONS CONTAINING NATURAL OIL GELS; and 60/900,518 filed Feb. 9, 2007 entitled NATURAL OIL SOFT-SOLID GELS, all of which are incorporated herein by reference.

STATEMENT REGARDING FEDERALLY SPONSORED RESEARCH

This invention disclosed herein was made partially with a grant # 2004-33610-14309 awarded by the U.S. Department of Agriculture, which has certain rights in this invention.

FIELD OF THE INVENTION

This invention relates generally to the compositions of novel clear and stable natural oil gels and novel stable natural oil soft solid gels as ingredients for health, cosmetic and beauty products, rinse-off personal cleansing products, and for household products such as candles, insect repellents, air fresheners, etc.

BACKGROUND OF THE INVENTION

Recently, there has been an urgent need to explore the use of natural plant oils, which are natural, green, biodegrable, and renewable, as alternative oils to the petroleum based oils. For example, biodiesel, which is methyl ester derived from renewable soybean oil and other renewable oils, has become the favored alternative oil to gasoline for consumers who are environmentally conscious. The present invention relates to the use of gelled natural plant or vegetable oils with block copolymers as alternative new raw materials to petroleum based raw materials for a wide range of applications including, but not limited to, candles, perfume delivery system, air care products, health, beauty, cosmetic and personal care products.

Block copolymers of polystyrene/rubber with molecular structures of diblock, triblock, radial, etc. are known in the arts and there are several commercial products. The most common rubber blocks are polyisoprene, polybutadiene, poly(ethylene-butylene), poly(ethylene-propylene), etc. Their commercial trade names include Kraton® by Kraton Polymer Inc., Vector® by Dexco Polymers Inc., Hybra® and Septon® by Kurray Inc.

These block copolymers are known to form oil gels with hydrocarbon oils of low solubility parameter. For example, the technical brochure of Kraton Polymer Inc—Fact Sheet K0026 Global, "Kraton Styrenic Block Copolymers in Oil Gels" described the oil gels of paraffinic or naphthenic oils with the G-series Kraton polymers whose rubber segments are saturated hydrocarbon polymers such as poly(ethylene-butylene), and poly (ethylene-propylene).

Fragrances, perfumes, pheromones, insect repellents, animal repellents, pesticide, and other volatile actives provide pleasant olfactory, health, and safety benefits through their release into air. Ways of controlling their delivery into air and onto the target areas have been proposed and practiced to enhance their functions and benefits in the prior art.

Despite these advancements, there is an on-going need for different ways of controlled-delivery of perfume and air-care actives in various consumer products.

To meet with increasing consumer demands, modern liquid and soft-solid personal cleansing products (shampoos, shower gels, facial cleansers, soap bars, etc.) must provide multiple benefits—good lathering characteristics, mildness to skin (non-drying), moisturization, sun protection, color protection, shine, aroma scent, long lasting perfume, and anti-aging, etc. in addition to the basic cleaning function.

SUMMARY OF THE INVENTION

The present invention is an article of manufacture, comprising a blend of: (A) from 1 to 50 weight percent of at least one block copolymer, wherein the block copolymer has at least one polystyrene block and at least one unsaturated rubber segment; and (B) from 99 to 50 weight percent of a natural oil. The natural oil of this invention is of natural animal, plant or vegetable oils or mixtures thereof, and the block copolymers have a polystyrene block and a rubber block where the rubber blocks are unsaturated rubbers such as polyisoprene, polybutadiene, or mixtures thereof. The block copolymers useful for the present invention are triblock polymers, radial (star) polymers, multiblock polymers, diblock polymers, or mixtures thereof.

One object of this invention is to provide a composition of a clear natural vegetable oil gel which exhibits advantageous properties for application in candles, perfume delivery, air care products, health cosmetic and beauty products, rinse-off personal cleansing products, personal care products, and household products.

Another object of this invention is to provide a composition of opaque natural vegetable oil soft solid gels which exhibit advantageous properties for application in candles, perfume delivery, air care products, health cosmetic and beauty products, rinse-off personal cleansing products, personal care products, and household products.

A further object is to provide compositions of an alternative green gel fuel based on the natural oil gels of the present invention as opposed to the fossil based hydrocarbon oil gel fuel for candles and other illuminating and heating applications.

An additional object of the invention is to provide a controlled-delivery composition of fragrance and air care actives comprising the clear natural vegetable oil gels or the opaque natural vegetable oil soft solid gels of the present invention.

Another objective of the present invention is to provide a composition of health, cosmetic, beauty, and personal care products comprising the clear natural vegetable oil gels or the opaque natural vegetable oil soft solid gels of the present invention.

Another objective of this invention is to provide a liquid or soft-solid personal cleansing composition comprising a hydrophobic benefit blend which comprises the clear vegetable oil gels and/or soft solid gels of vegetable oils of the present invention, and at least a lathering structured or non-structured cleansing phase comprising a surfactant component.

DESCRIPTION OF THE PREFERRED EMBODIMENTS

The block copolymers of this invention are composed of two incompatible blocks—polystyrene block and rubber block, and the two distinct polymer blocks are joined together by chemical bonds. The polystyrene block is thermoplastic, i.e. it is a solid plastic at room temperature and yet it is liquid at high temperature. The molecular structures for the copolymers are A-B-A for the linear triblock copolymers, $(A-B)_n$ for the radial block copolymers, and A-B for the diblock copolymers, where A is the polystyrene block, B is the rubber block, and n is >2 and less than 20. The B blocks of this invention are the unsaturated rubbers such as polyisoprene, polybutadiene, poly (isoprene-butadiene), poly(butadiene-styrene).

The block copolymer of this invention is selected from the group consisting of: polystyrene-polyisoprene-polystyrene, polystyrene-polybutadiene-polystyrene, polystyrene-poly (isoprene-butadiene)-polystyrene, polystyrene-poly(butadiene-styrene)-polystyrene, polystyrene-poly(ethylene-propylene-styrene)-polystyrene, polystyrene-polyisoprene, polystyrene-polybutadiene, polystyrene-poly(isoprene-butadiene), polystyrene-poly(butadiene-styrene), polystyrene-poly(ethylene-propylene-styrene) and mixtures thereof.

Examples of the commercial saturated block copolymers include, but are not limited to, Kraton® G polymers (by Kraton Polymers Inc. Houston, Tex.), and Septon® polymers (by Kuraray, Japan). Examples of the commercial unsaturated block copolymers include, but are not limited to, Kraton® D polymers and Vector® polymers (by Dexco Polymers), both of which have polybutadiene or polyisoprene as rubber blocks.

For convenience, the following abbreviations will be used to represent the block polymer structure: SBS: polystyrene-polybutadiene-polystyrene, SIS: polystyrene-polyisoprene-polystyrene, $(SB)_n$: radial polymer of polystyrene-polybutadiene, $(SI)_n$: radial polymer of polystyrene-polyisoprene, SI: polystyrene-polyisoprene, SB: polystyrene-polybutadiene, SEPS: polystyrene-poly(ethylene-propylene)-polystyrene, SEBS: polystyrene-poly(ethylene-butylene)-polystyrene.

The present invention is a composition which has a blend of: (A) from 1 to 50 weight percent of at least one block copolymer, wherein the block copolymer has at least one polystyrene block and at least one unsaturated rubber block; and (B) from 99 to 50 weigh percent of natural oil. The composition results in a clear natural oil gel.

The block copolymer portion of the invention represents from 1 to 50%, preferably from 5% to 30%, and most preferably from 5% to 25% by weight of the composition. The block copolymer can be a single block copolymer or a mixture of different block copolymers. The block copolymers have unsaturated rubber blocks, for examples, SBS, SB, SIS, SI, (SB)n, and (SI)n. The block copolymers have a polystyrene content from 5% to 80%, preferably from 10% to 50%, and most preferably from 15% to 40% by weight of the block copolymer. Examples of these copolymers include Kraton® D Polymers and Vector® polymers.

The natural oils of the present invention can be plant or animal oils, and tend to be liquid at the room temperature. They are extracted from a wide range of plants and animals. An example of animal oils is fish oil. The most preferred natural oils of the invention are plant or vegetable oils. For example a preferred vegetable oil is jojoba oil, which is a monoester of eicosanoic and docosanoic acids and eicosanol and docosanol alcohols. Most other vegetable oils are triglycerides of glycerin and fatty acids which are largely unsaturated fatty acids such as oleic acid and linoleic acid. The vegetable oils of the present invention include non-genetically modified oils, genetically modified oils, organic grown oils, non-organic grown oils, and mixtures thereof.

In general, vegetable oils are readily available and prepared by extraction from plant seeds. Examples of the vegetable oils or plant oils include, but are not limited to, almond, avocado, castor, coconut, corn, cottonseed, olive, peanut, rice bran, safflower, sesame, soybean, sunflower, walnut, canola, refined palm, meadaowfoam, tea tree oil, etc.

The clear natural oil gels of the present invention may additionally contain auxiliary ingredients including a) skin compatible hydrophobic emollients including, but not limited to, sensory enhancers, synthetic esters, and hydrocarbon oils, the preferred ones being those derived from natural oils; b) skin benefit agents; and c) colorants, fumed silica, cornstarch, antioxidants, etc.

Skin compatible hydrophobic emollients are defined as liquid at body temperature or bathing temperature and are deemed safe for use in cosmetics, i.e., they are either inert or actually beneficial to skin.

Synthetic ester oils contain at least one ester group. Non-limiting examples include fatty acid mono and polyesters such as cetyl octanoate, myristyl lacatate, isopropyl myristate, glyceryl distearate, alkyl citrate, alkyl tartrate, sucrose ester, sorbitol ester, caprylic/capric triglyceride, and the like. Other classes of non-limiting examples are liquid polyesters from the reaction of a dicarboxylic acid and a diol, such as PURESYN ESTERS® from Exxon Mobil. The preferred ones are those derived from natural oils.

Liquid hydrocarbons are a further class of skin compatible emollients. These include linear and branched oils such as liquid paraffin, squalene, mineral oil, and low viscosity synthetic hydrocarbons such as polyalphaolefins sold by Exxon-Mobil under the trade name PANALENE® or INDOPOL®. Skin compatible emollients also include petrolatum jelly, which is a blend of mineral oil, paraffin waxes, and microcrystalline waxes. Silicone based skin compatible emollients are also desirable. They include linear and cyclic polydimethylsiloxane, organo functional silicones, and aminosilicones.

The naturally derived skin compatible emollients are defined as having at least a part of their molecule originate from natural oils or natural resources. Non-limiting examples include caprylic/capric triglyceride (CCTG), isopropyl palmitate, octyl palmitate, sucrose esters, sorbitol esters, polyesters derived from castor oils, squalene, alkyl citrate, etc. CCTG is a natural component of coconut oil and can also be synthesized.

Skin benefit agents function to improve the state of skin by prevention and repair and include the following: a) fragrances that provide in-use and after-use pleasant smells; b) Vitamins and vitamin alkyl esters, including vitamin C, vitamin E, vitamin B, etc.; c) UV filters that block the sun's harmful UV rays such as octyl methoxy cinnamte, butylmethoxy benzoylmethane, ultra-fine $TiO_2$, ZnO, and their mixtures; d) Skin lightening agents used to increase the lightness of the skin such as niacinnamide; e) Antimicrobial agents such as triclosan; f) Anti-oxidants used to reduce photodamage and premature damage due to excessive oxidation such as ascorbyl palmitate, vitamin E acetate, butylated hydroxyanisole, and 2,6-ditertiarybutylpara-cresol.

In general, the clear natural vegetable oil gels are prepared by blending the block copolymers and the natural oils at 100° C. to 250° C. under slow or moderate mixing speed. Once the blends become a homogeneous and clear solution, they are cooled down to room temperature, resulting in clear gels. The natural vegetable oil gels of the present invention are stable and clear. Their clarity is such that one can read the black words on white paper through a gel of 1 cm thickness. On the other hand, the natural vegetable oil gels made of natural vegetable oils and the block copolymers with saturated rubber segments become opaque with separation of oil and gel over a short period of time.

It is recognized by those skilled in the art that by varying the concentration, molecular weight, and types of block copolymers, there can be prepared a wide range of the natural vegetable oil gels with physical and mechanical properties ranging from strong gels that are elastic, difficult to deform or to break, to weak and soft gels that can be deformed or broken with a minimum force, and to thickened viscous oils with viscosity over 1,000 cP at 5 rpm.

In another embodiment of this invention, an opaque natural oil soft solid gel is formed by combining the clear natural vegetable oil gels of the present invention with skin compatible solid waxes. The skin compatible solid waxes are selected from the group consisting of beeswax and beeswax derivatives, hydrogenated vegetable oils and their derivatives, vegetable waxes and their derivatives, sterols and cholesterol fatty acid esters, phospholipids, sphingo lipids, ceramides, glycoshingo lipids, synthetic ester waxes, solid fatty acids and fatty alcohols and their derivatives, stearic acid, behenyl alcohol, glyceryl monostearate, solid synthetic alcohols, microcrystalline waxes, paraffin waxes, ozokerite, polyethylene, silicone waxes, and mixtures thereof. Also included are shell waxes, butters (Shea, cocoa, etc), alcohols and acids of $C_{12-50}$ alcohols.

The said opaque natural oil soft solid gel may additionally contain skin compatible emollients, skin benefit agents, colorants, etc.

In general, the opaque natural vegetable oil soft solid gels of this invention are prepared by blending the clear natural vegetable oil gels, skin compatible waxes, and auxiliary additives together at 100° C. to 250° C. under slow or moderate mixing speed until homogenous, then cooled to room temperature. Alternatively, they can also be prepared directly from a blend of block copolymers, natural vegetable oils, skin compatible waxes, and auxiliary additives.

The total weight of block copolymer in the opaque soft solid gels of this invention ranges from 1% to 60%, preferably from 2% to 40%, and most preferably from 2% to 30%. The total % by weight of solid waxes ranges from 1% to 60%, preferably from 5% to 40%, and most preferably from 5% to 30%. The total % by weight of natural oil ranges from 5% to 95%, preferably from 20% to 90%, and most preferably from 40% to 90%.

The solid waxes are solid at room temperature with melting temperature from 35° C. to 180° C. Non-limiting examples of the waxy materials include beeswax, beeswax derivatives; hydrogenated vegetable oils, their derivatives; vegetable waxes such as carnauba and candelilla waxes, their derivatives; sterols such as cholesterol, cholesterol fatty acid esters; phospholipids such as lecithin and derivatives, sphingo lipids, ceramides, glycoshingo lipids, etc; synthetic ester waxes such as stearyl stearate; solid fatty acid, fatty alcohols, and their derivatives, such as stearic acid, behenyl alcohol, glyceryl monostearate; synthetic alcohols and fatty acids and their derivatives, such as Unilin® and Unithox® lines from Petrolite, Syncrhrowax® from Croda, etc; microcrystalline waxes; paraffin waxes; ozokerite, polyethylene, silicone waxes, etc. The preferred waxes are selected from natural origins such as beeswaxes, hydrogenated vegetable oils, natural fatty acid and fatty alcohols and their derivatives.

Although not to be limited by any theory, it is believed that solid waxes such as vegetable waxes structure vegetable oils via an interlocking network of macroscopic crystals, whereas the block copolymers of the present invention structure vegetable oils by a network of micro-domains of polystyrene. Combination of the two structuring mechanisms or materials in the opaque soft solid gels of the present invention results in a unique material with properties different from the clear vegetable oil gels of the present invention and the gels of vegetable waxes and vegetable oils.

Today's candles are bought for their decorative elements and their scents in addition to their warm illumination. In other words, they are for fun, pleasure, mood, and emotional needs. A growing consumer segment prefers candles made of renewable, environmentally-safe (often referred to as 'green') and friendly resources. Another embodiment of the present invention is to provide an article of manufacture of a 'green' candle or 'green' solid fuel, using the clear or opaque natural oil gels of the present invention, to meet with this growing consumer need.

The natural oil gel candle of this invention comprises: a) the opaque natural vegetable oil soft solid gels or clear natural oil gels of the present invention; b) a wick in the gel; c) additives selected from the group of fragrance, stabilizer, antioxidant, flame retardant, colorant, insect repellent, insoluble decorative objects, etc.; and d) optionally, other oils derived from natural vegetable oils, and hydrocarbon oils. Examples of optional oils derived from vegetable oils include biodiesels, isopropyl palmitate, stearic acid, glyceryl stearate, octyl palmitate, etc. The optional hydrocarbon oils include mineral oils, paraffinic oil, naphthenic oil, etc. Depending on how the colorants are applied, the gel candle can be one color, multicolor, colored layers, etc.

The candles of the present invention can be a conventional solid free-standing candle or a gel candle in container. It is understood that single or blends of diblock, triblock, multi-block and radial block copolymers in various ratios in the natural vegetable oils can be used to develop the different set of the desired mechanical, physical, and optical properties for the different kinds of candles such as free standing candle, gel candle, etc.

A preferred article of manufacture is a clear container gel candle, comprising a) a clear natural oil gel of the present invention where the natural oil gel is a vegetable oil; b) a wick in the gel; c) a clear container, with gel candle in the container; d) additives selected from the group of fragrance, stabilizer, antioxidant, flame retardant, colorant, insect repellent, insoluble decorative objects and e) optionally, oils derived from natural vegetable oils, and hydrocarbon oils, and mixtures thereof, with the proviso that the gel remains clear.

The gel candle of the present invention can be prepared by heating the clear natural vegetable oil gels of the present invention to about 70-100° C., blending with additives such as fragrance, dye, pigments, etc., and inserting the wick and insoluble decorative objects before solidification. On cooling down to room temperature, the free-standing gel candle or container gel candle forms.

Another embodiment of the present invention is to provide a composition for the controlled-delivery of fragrances and air care products, comprising a delivery blend of natural vegetable oil gels of the present invention and fragrance and air care actives, for the growing consumer segment that prefer products from renewable and environmentally-friendly resource.

The controlled-delivery natural oil gel composition of fragrance and air care actives of the present invention have a delivery blend of the clear or opaque natural oil gels of the present invention, fragrance and air care actives, and auxiliary additives. The delivery blend is from a) 99 weight percent to 10 weight percent of the clear or opaque natural oil gels of the present invention, b) from 1 weight percent to 90 weight percent perfume and air care actives, and c) optional auxiliary additives selected from the group consisting of colorants, solubilizer, stabilizer, volatile oils, emulsifiers, sensory enhancer, etc.

The fragrances, perfume and air care actives useful to the composition of this invention are selected from the group consisting of fragrances, essential oils, deodorizers, masking agents, pest repellents, pesticides, etc., and mixtures thereof. Included are synthetic fragrances and other air care actives that are soluble in natural oils. Fragrances include, but are not limited to, perfumes, essential oils, extracts, absolutes, resinoids, concentrates, and mixtures thereof. Examples include terpenic hydrocarbons, esters, ethers, alcohols, aldehydes, ketones, acetals, and derivatives thereof and mixtures thereof. Other examples include fruit scents such as almond, grape, orange, raspberry, etc.; flower scents such as lavender, rose-like, carnation-like, rosemary, thyme, etc.; woodland scents such as pine, spruce, etc.; essential oils such as peppermint, spearmint, etc.

For those skilled in the art, such fragrances and perfumes useful to this invention can be found in S. Arctander, "Perfume and Flavor Chemicals" (Montclair, N.J., 1969), in S. Arctander, "Perfume and Flavor Materials of Natural Origin" (Elizabeth, N.J., 1960), "Perfumes Cosmetics and Soap", $2^{nd}$ edition, edited by W. A. Poucher, 1959, and in "Flavor and Fragrance Materials—1992", Allured Publishing Co. Wheaton, Ill., incorporated herein by reference.

The insect repellent, pest repellent, and pesticide actives useful to the present invention can repel or terminate harmful or destructive organisms such as insects, nematodes, fungi or the like. Examples of insect repellents include, but not limited to, N, N-diethyl-m-toluyamide (DEET) for mosquito, E-empenthrin for moths, and citronella oil. Examples of pesticides include, but are not limited to, N-[[(4-chlorophenyl)-amino] carbonyl]-2,6-difluorobenzamide; 2,2-dimethyl-1,3-benzodioxol-4-yl) methylcarbamate; O,O-diethyl-O-6-methyl-2-(1-methylethyl)-4-pyrimidinyl phosphorothioate; and O-ethyl-5-phenyl ethylphosphonodithioate. Other examples include: baits and stomach kills such as Hydromethylnon, Fenoxycarb, and Avermectin; residual contact kills such as Pyrethroids, Carbamates, and Phosphorothioates; Fumigant kills such as organophosphates, Crysanthemums, Juvenile Hormones.

The auxiliary additives may be incorporated to an extent not negatively affecting the controlled delivery objectives. For example, colorants can be used to impart single or multicolor to the gels, and antioxidants such as BHT and flame retardants can also be incorporated to enhance stability and safety. Volatile oils such as cyclopentasiloxane, isododecane, etc. may enhance the controlled delivery.

The method of preparation for the said delivery blend may include: heating the natural oil gels of the present invention to 60-110° C., blending in air active actives and auxiliary additives, and cooling down in a mold to form a desired shape.

It is recognized by those skilled in the art that the composition comprising the said delivery blend can include a wide range of finished products. The said delivery blend can be spray-cooled to form powders, emulsified into hydrophilic media to become an emulsion or dispersion, and formulated into a conventional aerosol spray container using hydrocarbon propellants such as dimethyl ether, and that the resulting powder and dispersions can be manufactured into a wide range of health, cosmetic, beauty, personal care, personal cleansing, household, and agricultural finished products. Thereby, the compositions of these finished products can comprise the said delivery blend.

For example, an air freshener apparatus that is powered by a heating element may comprise the delivery blend of the present invention.

Another example is the hydrophilic dispersion or emulsion of the delivery blend; it can have particles of the delivery blend from 10% by weight to 80% by weight in the carriers such as water, and most preferably from 40% to 75%. The particle size can be from 0.1 u to 5000 u, and preferably from 1 u to 1000 u. The dispersed particles can carry neutral, negative, positive, or zwitterionic charges by using emulsifiers with neutral, negative, positive, and zwitterionic charges; the preferred charge is a net positive charge by using cationic emulsifiers, or mixtures of cationic, nonionic, and zwitterionic emulsifiers. Another preferred method of imparting positive charges to the dispersed particles is to coat the dispersed particles with cationic polymers.

Anchoring cationic polymers onto the particles of the delivery blend can be accomplished by physical bondings such as hydrogen interaction, ionic interaction, or hydrophobic interaction, or by chemical bonding to form permanent chemical bonds to the gel particles.

It is recognized by those skilled in the art that a wide range of water soluble cationic, amphoteric polymers or mixtures thereof can be used for this invention. Examples include polysaccharide, polypeptide, polyacrylate, aminosilicone, etc. Other suitable water soluble polymers are provided in U.S. Pat. No. 7,196,049, and U.S. Pat. No. 7,122,512, which are incorporated herein by reference.

These types of hydrophilic dispersions comprising the said delivery blend can be manufactured into leave-on products, rinse-off products, fabric detergents, fabric softeners, bar soaps, pest control products, etc.

Non-limiting examples 6-8 illustrate a wide range of compositions of different finished products.

Natural oils such as olive oil, coconut oil, sesame oil, etc. are important ingredients for formulating modern health, cosmetic, beauty, personal care, and personal cleansing products. These products, which remain on the skin and hair after application, include skin creams, lipsticks, lip balms, foundations, deodorants, hair treatment gels and conditioners, pharmaceutical topical treatment ointments and creams, sunscreens, color cosmetics, etc. and can be referred to as "leave on" products. Other products, which are rinsed off after application, include shower gels, shampoo, bar soap, facial cleanser, hand cleanser, etc. and can be referred to as "rinse-off" products. However, the natural oils are liquid, and do not always meet with many formulation needs of these modern "leave on" and "rinse off" health, cosmetic, beauty, personal care, and personal cleansing products.

The clear natural vegetable oil gels and the opaque natural vegetable oil soft solid gels of the present invention are compatible with essentially all of these natural oils, and common emollients, skin actives, and auxiliary ingredients. They enhance the viscosity, tactile property, formulation flexibility, substantivity, wear-resistance, transfer-resistance, water-resistance, and other benefits of natural oils on skin and hair.

The composition of the leave-on health, beauty, cosmetic, and personal care products of the present invention comprises the said clear natural vegetable oil gel and/or the said natural vegetable oil opaque soft solid gels form 100% to 1%, preferably from 50% to 2%, and most preferably from 20% to 5%, and the remaining % being the health and cosmetically acceptable active, functional, inert and auxiliary ingredients. The said actives and benefit agents are selected, but are not limited to, from the group of skin moisturizers, emollients, synthetic ester oils, skin whitening agents, vitamins, anti-oxidants, blood clotting agents, wound healing agents, absorbents for wounds, antibacterial, hair conditioner, UV filters, anti-aging agents, etc. The said functional and auxiliary ingredients include, but are not limited to, cleansing surfactants, emulsifiers, emollients, synthetic ester oil, synthetic hydrocarbon oils, fragrance, colorants, preservatives, and other suitable carriers such as water, glycerin, etc.

The "leave-on" health, beauty, cosmetic, and personal care products of the present invention can be in many different formats including, but not limited to, anhydrous, emulsion ("wipe-on", or "wipe-off"), cream, lotion, gel, ointment, stick, spray-on, paste, power, etc. Non-limiting examples 8-12 further illustrate the compositions of the leave-on products.

Another embodiment of this invention is to provide a liquid or soft solid personal cleansing composition that comprises at least a hydrophobic benefit blend, having either/or the clear vegetable oil gels and/or the opaque natural oil soft solid gels of the present invention, and at least a lathering structured or a lathering non-structured cleansing phase having a surfactant component.

The hydrophobic benefit blend of the present invention comprises the clear natural vegetable oil gels, the opaque natural vegetable oil soft solid gels of the present invention, skin compatible emollients, skin compatible waxes, skin benefit agents, and optionally auxiliary agents such as pigments, colorants, etc. The preferred composition preferably comprises 10% to 100% of the natural oil gels of the present composition, and 90% to 0% of the skin compatible emollients and waxes, skin benefit agents and auxiliary agents; and most preferably comprises 20% to 100% of the said gels and 80% to 0% of other components. The said benefit blends of this invention range from soft gels to soft solids to liquids with good consistency.

The cleansing phase comprises a surfactant component, and preferably has structures which exhibit shear thinning rheology with adequate yield stress or yield point to stabilize the hydrophobic benefit domain and multiphase product format. The said structured cleansing phase comprises liquid crystalline surfactant phase which is formed by blending the surfactant components with suitable liquid crystalline inducers, stabilizers, and mixtures thereof. The cleansing phase further comprises cationic deposition polymers, pigments, shiny particles, electrolyte, preservatives, fragrance, exfoliate particles, water soluble skin benefit agents, beads, humectants, pH regulators, etc.

The surfactant component comprises a surfactant or a mixture of surfactants; these surfactants are suitable for application to the skin and hair, and include herein any known or otherwise effective cleansing surfactant suitable for application to skin and hair, and which is otherwise compatible with the other essential ingredients in the stable multi-phased personal care composition. These surfactants include linear or branched anionic, nonionic, cationic, zwitterionic or amphoteric surfactants, soap, or combinations thereof. The % by weight of surfactant component in the cleansing phase can range from 2% to 90%, preferably from 5% to 40% and more preferably from 10% to 30%.

Examples of these liquid crystalline inducers include linear or branched fatty acids, ester derivatives thereof, linear or branched fatty alcohols, lauric acid, isostearic acid, glyceryl isostearate, etc. U.S. Pat. No. 6,067,816 (2000), U.S. Pat. No. 6,426,326 (2002), U.S. Pat. No. 5,952,286 (1999), and US 2006/0079417 A1, teach the art of forming the said lamellar surfactant phase with the said liquid crystalline inducers and are incorporated herein by reference.

The stabilizers also enhance the overall product stability by providing additional structuring, and they include thickeners selected from a group consisting of clays, deflocculating polymers, synthetic polymers, naturally derived polymers, crosslinked polymers, associative polymers, hydrophobically modified polymers, etc. Examples of these thickeners useful for the present invention are disclosed in U.S. Pat. Nos. 4,509, 949 and 2,798,053; and CTFA International Cosmetic Ingredient Dictionary, fourth edition, 1991, pp. 12 and 80, all of which are incorporated herein by reference. Non-limiting examples include clay, silica, starch, hydroxypropylphosphate starch, starch octenyl succinate, alginates, pectin, carageenans, gum Arabic, guar gum, xanthan gum, hydroxypropylcellulose, chitosan, gelatin, casein, cross-linked polyacrylate, cross-linked polyacrylamide, acrylates/beheneth-25 methacrylate copolymer, etc.

Another class of the said stabilizer is selected from hydroxyl-containing crystalline substance such as hydroxyl-containing fatty acid, fatty ester or fatty soap, particularly trihydroxystearin.

Those skilled in the art recognize that the compositions of the present composition can exist in a number of product formats including but not limited to liquid personal cleansing products such as shower gels, shower gels with visibly distinguishable stripes or phases, facial washing creams, cleansing foams, shampoos, etc. and soft solid personal cleansing products such as bar soaps and syndet bars.

Another embodiment of the present invention in the form of a personal cleansing product is a soft solid soap bar and a mild cleansing syndet bar comprising particles of a hydrophobic benefit domain comprising the clear natural vegetable oil gels and/or the opaque natural vegetable oil soft solid gels of the present invention. The compositions of the soap bar and syndet bar comprise 20% to 90% by weight of soap, mild lathering surfactants, and mixtures thereof, 2% to 50% by weight of the hydrophobic benefit domain of the present invention, and 3 to 20% by weight of binders selected from the group of water, liquid water-soluble aliphatic polyol, polyethylene glycol, polypropylene glycol, and mixtures thereof. Preferably, the compositions comprise 20% to 90% by weight of soap, mild lathering surfactants, and mixtures thereof, 2% to 30% by weight of the hydrophobic benefit domain of the present invention, and 3 to 20% by weight of binders.

EXAMPLES

The vegetable oil gels in Examples 1 and 2 were prepared using the following procedure. First, 80 parts by weight of soybean oil were added to a glass beaker and heated to a temperature of between 100° C. to 200° C. Then, 20 parts by weight of either the Kraton® 0 block copolymers (available from Kraton Polymers, US, Houston, Tx.) or Vector® block copolymers (available from Dexco Polymers, US, Houston, Tex.), were mixed in with an overhead mixer until the solution became visibly clear. The solution was cooled down and transferred to a clear plastic jar for a stability test. After three days at room temperature, the vegetable oil gels were evaluated by three criteria: clarity, oil bleeding, and mechanical properties. The clarity or transparency is judged by one's ability to read the black words on white paper through a gel of 1 cm thickness. The oil bleeding is judged by a separated and visibly clear oil layer on top of the gel. The mechanical properties including stickiness, softness, and elasticity are judged by touching and stretching the gels with fingers and hands. The percent given for a component in the following examples is by weight.

A successful gel is judged to be clear and has no oil bleeding. For convenience, the following acronyms are used to represent the block polymer structure:

| | |
|---|---|
| SBS | polystyrene-polybutadiene-polystyrene |
| SIS: | polystyrene-polyisoprene-polystyrene |
| (SB)$_n$ | radial polymer of polystyrenepolybutadiene |
| (SI)$_n$ | radial polymer of polystyrene-polyisoprene |
| SI | polystyrene-polyisoprene |
| SB | polystyrene-polybutadiene |
| SEPS | polystyrene-poly(ethylene-propylene)-polystyrene |
| SEBS: | polystyrene-poly(ethylene-butylene)-polystyrene |

Example 1

Stable Clear Natural Vegetable Oil Gels of this Invention

This example demonstrates the clear vegetable oil gels of the present invention using block copolymers with unsaturated rubber segments. Kraton® D polymers and Vector® polymers are block copolymers of polystyrene and unsaturated rubbers such as polyisoprene and polybutadiene. Regardless of their polymer micro-structures and molecular weight (as indicated by the viscosity, measured at 25% by weight in toluene and room temperature), all Kraton® D and Vector® block copolymers were able to gel soybean oil successfully to stable clear gels whose mechanical property ranges from soft gel, to medium elastomer, and to hard elastomer.

TABLE 1

Stable Natural Oil Gels from Blends of Soybean Oil and Kraton D/Vector Polymer

| Kraton ® D | Polymer structure | % polystyrene | Viscosity, cP | Oil bleeding | Clarity | Mechanical property |
|---|---|---|---|---|---|---|
| D1102 | SBS | 28% | 1200 | None | Clear and | Soft and flow- |
| D1161 | SIS | 15% | 1200 | None | Clear and | Soft and flow- |
| D1113 | SIS | 16% | 600 | None | Light yellow, | Soft and flow- |
| D1112 | SIS | 15% | 900 | None | Light brown, | Soft and flow- |
| D1119 | SIS | 22% | 340 | none | Light yellow, | Soft elastomer |
| D1193 | SIS | 24% | 400 | None | Clear and | Medium |
| D1133 | SBS | 35% | 400 | None | Clear and | Medium |
| D1124 | (SI)n | 30% | 340 | None | Clear and | Medium |
| D1184 | (SB)n | 31% | 20000 | None | Translucent | Strong elastamer |
| D1155 | (SB)n | 39% | 700 | None | Clear and | Medium |
| D1144 | (SB)n | 31% | — | none | Clear and | Strong elastamer |
| V4411 | SIS | 44 | 120 | None | Clear and | Soft and easy to |
| V4211 | SIS | 30 | 300 | None | Light brown | Soft, sticky, easy |
| V4111 | SIS | 18 | 880 | None | Clear and | Soft, sticky, |
| V8505 | SBS | 29 | 400 | None | Clear and | Soft to medium |
| V4461 | SBS | 43 | 850 | None | Clear and | Medium |
| V2518 | SBS | 31 | 1200 | None | Clear and | Strong elastamer |
| V2411 | (SB)n | 30 | — | None | Clear and | Strong elastamer |
| V4230 | (SI)n | 20 | — | None | Clear and | Medium |

Example 2

Comparative Examples of Unstable Natural Vegetable Oil Gels

Table 2 shows the results from blends of Kraton® G block copolymers and soybean oil. Kraton® G polymers have saturated rubber blocks as poly(ethylene-propylene) or poly(ethylene-butylene). Regardless of whether the copolymer was a triblock or diblock copolymer, none of the Kraton polymers having saturated rubber blocks successfully blended with the soybean oil to form a stable and clear gel; instead, all gels were opaque with oil bleeding. Thus, in order to form the gels of the present invention, the gels must be prepared using copolymers having unsaturated rubber blocks.

TABLE 2

Unstable Natural Oil Gels from Blends of Saturated block copolymers - Kraton ® G and Soybean oil

| Product code | Polymer structure | % of polystyrene | Viscosity in toluene. | Oil bleeding | Clarity | Mechanical property |
|---|---|---|---|---|---|---|
| G1650 | SEBS | 30% | 8000 | Small | Opaque | Elastic |
| G1652 | SEBS | 30% | 1,800 | Small | Opaque | Elastic |
| G1651 | SEBS | 33% | >50,000 | Large | Opaque | Elastic |
| G1657 | SEBS | 13% | 4,200 | Large | Opaque | Strong |
| G1702 | SEP | 28% | >50,000 | Medium | Opaque | Soft waxy |
| G1701 | SEP | 37% | >50,000 | Medium | Opaque | Soft waxy |

Example 3

Stable Opaque Natural Oil Gels of this Invention

This example demonstrates the composition of opaque soft solid natural vegetable oil gels of the present invention. They were characterized by the physical properties of ease of tearing, stickiness, and bounce/elasticity with a subjective scale of 1-5 by using fingers and hands to touch and stretch the gels. In comparison to the clear vegetable oil gels of the present invention, these opaque soft solids are as stable but less sticky and more pliable.

TABLE 3

Stable Opaque soft solid of natural vegetable oil gel

| | #1 | #2 | #3 | #4 |
|---|---|---|---|---|
| Krayton ® D1118 | 15% | 7.5% | 6% | 10% |
| Hydrogenated Soya oil wax | | 15% | | 25% |
| Glyceryl monostearate | | | 15% | |
| Candillia wax | 5% | | | |
| Soya oil | 80% | 77.5% | 79% | 65% |
| Ease of tearing apart | 2 | 4 | 4 | 2 |
| Stickiness | 3 | 2 | 1 | 3 |
| Bounce/elasticity | 5 | 4 | 3 | 5 |

Example 4

Stable Natural Oil Gels Containing Skin Compatible Emollients

This example illustrates that the compositions of stable natural oil gels of this invention, comprising skin compatible emollients in addition to the natural vegetable oil. These gels were prepared by the method described above. Those skilled in the art recognize that the % by weight of the skin compatible emollients can be up to the level that the final gels remained stable and that this % level would vary depending on the % and types of copolymers of this invention.

TABLE 4

Natural oil gels with skin compatible emollients

| | #1 | #2 | #3 |
|---|---|---|---|
| V4411 | 15% | 15% | 15% |
| Octyl palmitate | 45% | | |
| Caprylic/Capric Triglyceride | | 10% | |
| Isononyl Isononoate | | | 45% |
| Sunflower seed oil | 40% | 75% | 40% |
| Appearance | clear | Clear to translucent | clear |

TABLE 4-continued

Natural oil gels with skin compatible emollients

| | #1 | #2 | #3 |
|---|---|---|---|
| Mechanical property | Medium elastomer | Medium elastomer | Medium elastomer |

Example 5

Clear Container Gel Candle

A blend of 99% by weight of clear natural vegetable oil gel consisting of 20% of Vector® V4411 block copolymer, 80% Soya oil from Table 2 and 1% of citronella oil are heated to 80° C., and poured into a clear glass container with a standard wick inside. The wick is held in place as the blend cools down to room temperature, resulting in a clear container gel candle. This candle burns evenly for several hours.

The following examples illustrate the various compositions comprising the natural oil gels of the present invention and air care actives for a wide range of products.

Example 6

Air Freshener and Insect Repellent

A clear and transparent gel of 60% Soya oil and 40% Vector® 4411 block copolymer was prepared by the procedures described above. An insect repellant/air freshener of 80% of the prepared gel and 20% of the citronella oil was prepared by heating the gel to 90° C., then adding the citronella oil, then mixing quickly to a visibly clear solution. It was poured into a round mold of alumina dish while it was liquid. It cooled down to become a clear and transparent round gel; and the citronella smell was released into air slowly and continuously for several days. This example illustrates the composition in gel form.

Example 7

Long Lasting Fragrance Cream

A cream was made having a Phase A: 59% water, 3% glycerin, 1.5% Guar Hydroxypropyltrimonium Chloride; and Phase B: 5% Steareth-21, 1% Distearyldimonium Chloride, 35% of a mixture of 5% fragrance and 95% of a natural vegetable oil gel (20% Vector 4411 and 80% soybean oil). The fragrance is "Rain Shower" by Belle Aire. The cream was prepared by heating the phase A and B separately to 75° C., followed by mixing Phase B into Phase A. The cream was soft and shining. After applying to skin, it dried to form a film with a pleasant smell continuously detectable for several hours.

Example 8

Shampoo with Lasting Pleasant Smell

This composition was prepared by mixing 70.85% of water, 10% of sodium lauryl ether sulfate (70%), 7% of cocamidopropyl betain (35%), 0.5% of cocamide MEA, 0.05% disodium EDTA, 0.3% PEG150 distearate, and 1% sodium chloride at 75° C. to a clear solution, followed by blending 0.3% of preservatives, and 10% of the cream from example 6. This shampoo was a white cream, generating foams easily and having a lasting pleasant smell. This example illustrates that the composition can be incorporated into a wide range of product formats such as skin care, personal care, color cosmetics, personal cleansing, etc. to provide lasting pleasant smell in addition to the intended primary benefits of the products.

The following examples illustrate the composition of various health, beauty, and cosmetic products, comprising the natural vegetable oil gels of the present invention, and skin/health actives and auxiliary ingredients. These products include, but are not limited to, skin care, sun care, hair conditioner, body oil, in-shower body moisturizer, foundation, etc.

Example 9

Sesame Body Oil

This preparation was made by blending 40% of the natural vegetable oil gel of this invention (10% Krayton® D4411 and 90% sesame oil), 20% Sesame oil, 40% isopropyl myristate, 5% PEG-40 sorbitan peroleate, and fragrance at 70° C. to a clear solution. After cooling down, it was liquid with some consistency. It spread over skin very easily and absorbed into skin quickly, leaving skin feeling soft and velvety with no greasy feel at all.

Example 10

Sesame Glossing Hair and Skin Serum

This composition was prepared by blending 40% of the natural vegetable oil gel of this invention (10% Kraton® D1118 and sesame oil), 30% sesame oil, 14% cyclopentasiloxane, 12.5% isopropyl myristate, 2% PEG 40 sorbitan peroleate, 1.5% dimethicone copolyol, and a few drops of fragrance at 70° C. to a clear solution, followed by cooling down to a thin liquid soft gel. When applied to skin or hair, it felt very soft on contact, absorbed into skin quickly, and left skin and hair soft and shining.

Example 11

Body Butter with Natural Oils

These body butter compositions were prepared by the normal procedures of cosmetic products such as the procedures of example 6. They were all soft creams, spreading over skin easily and leaving skin feeling soft and moisturized by the natural plant oils. The said body butters exhibited a soft and bouncy tactile when they were applied to skin; this is believed to be due to the bouncy nature of the natural oil gels of the present invention.

TABLE 4

| Ingredients | #1 | #2 | #3 |
|---|---|---|---|
| O/W Body Butter | | | |
| Phase A | | | |
| Water | 60.85% | 53.85% | 58.15% |
| Glycerine | 6% | 6% | 6% |
| Caramel color (2% solution) | | 2% | 1% |
| Xanthan gum | 0.5% | | 1.2% |
| Hydroxypropyl starch phosphate | 2% | 2.5% | |
| Dosodium EDTA | 0.05% | 0.05% | 0.05% |
| Phase B | | | |
| Soft solid natural vegetable oil gel, # 4 of | 10% | 10% | 10% |
| Sunflower oil | 5% | 4% | 2% |
| Vegetable Shortening | 9% | | |
| Shea Butter | | 8% | 10% |
| Caprylic/Capric Triglyceride | | 2% | |
| Dimethicone oil | | 1% | 1% |
| Cyclopentasiloxane | | 5% | 5% |
| Beeswax | 2% | | |
| Cetearyl alcohol | 3% | 3% | 3% |
| GMS/PEG-100 stearate | 1.5% | 2% | 2% |
| Phase C | | | |
| Preservative, perfume | Q.S. | Q.S. | Q.S. |

Example 12

Foundation with Natural Vegetable Oil

This composition was a water-in-oil emulsion, and was prepared by mixing the water phase into the oil phase. The composition break-down: oil phase—6% of # 4 natural oil gel soft solid of Table 3, 6% Shea Butter, 6% sunflower oil, 1.5% PEG-30 dipolyhydroxystearic acid, 0.12% polyhydroxystearic acid, 0.4% sorbitan oleate, 3% cyclopentasiloxane, 1% dimethicone oil, 12% pigment mixture of white titanium dioxide, yellow, red, and black iron oxide, and 2% mica; oil phase—55.13% water, 5% glycerin, and auxiliary additives including magnesium sulfate, preservative, and perfume.

The following examples illustrate the compositions comprising (a) the natural vegetable oil gels of this invention, and (b) a cleansing phase. Examples of these products include, but are not limited to, shower gel, shampoo, facial wash, fabric washing detergent, car washing detergent, bar soap, syndet bar, etc.

Example 13

Moisturizing Shower Gels with the Natural Vegetable Gels

These compositions were prepared by the conventional method. The benefit domain was prepared similar to the examples 1 and 2. The cleansing phase was prepared with an overhead mixer by mixing the ingredients in a beaker at a moderate speed at 70-80° C. The hydrophobic benefit phase at 50-70° C. was mixed into the cleansing phase in the beaker. All formulations were soft lotion or cream products, were very easy to spread over skin, and they generated rich foams. After the wash, the skin felt very soft and velvety, and had a pleasant smell. The cleansing phase of the #3 composition was a lamellar phase.

TABLE 5

Moisturizing Shower Gels with Natural Oil Gels

| Ingredients | #1 | #2 | #3 |
|---|---|---|---|
| Cleansing Phase | | | |
| Water | To 100% | To 100% | To 100% |
| Carbomer (Ultrez 20) | 0.5% | 0.2% | 0.25% |
| Hydroxypropyl Starch Phosphate | | 0.8% | 1% |
| Sodium Lauryl ether sulfate @70% | 11.8% | 11.8% | 10% |
| Cocamidopropyl Betaine @30% | 7.9% | 7.9% | 8% |
| Cocamide MEA | 1% | 1% | |
| Disodium EDTA | 0.04% | 0.04% | 0.04% |
| Lauric acid | | | 3% |
| TiO2 | | 0.1% | |
| Glycerine | | 2% | |
| Guar Hydroxypropyltrimonium Chloride | 0.15% | 0.15% | 0.15% |
| Glycerine | 4.00% | 4% | 4% |
| 18% Sodium Hydroxide | 0.84% | 0.36% | 0.42% |
| Preservative | 0.3% | 0.3% | 0.3% |
| Perfume | 0.2% | 0.6% | |
| Hydrophobic Benefit Phase | | | |
| Gel of 10% Kraton D1118 and 90% soya | 3% | 6% | 3% |
| Caprylic/capric triglyceride | | 1% | |
| Soya oil | 2% | 3% | |
| Sunflower oil | | | 2% |
| Perfume | | | 0.6% |
| Viscosity, cP at 5 rpm, | 53,000 | 25,000 | 108,000 |

Example 14

Conditioning Shampoos with Natural Oils

The composition was prepared by first mixing together 70.65% water, 0.2% guar hydroxypropyltrimonium chloride, 1% glycerin, 7% sodium lauryl ether sulfate (70%), 10% Cocamidopropyl Betaine @30%, 0.5% Cocamide MEA, 0.05% disodium EDTA, 1% sodium chloride, and 0.3% PEG-150 distearate at 75 C, followed by 3% of a mixture of 33% soya oil gel of this invention (20% Vector 441/80% soya oil) and 67% of olive oil, and preservatives and perfumes. This shampoo washed the hair with good foaming action and left the hair soft and conditioned.

Example 15

Moisturize Body Shower Lotion for Dry Skin

This composition is for conditioning and moisturizing dry skin while it is wet in the shower. It was a stable lotion that spreads over the wet body skin easily. After rinsing with water and drying the body with a towel, the skin felt moisturized and renewed. It was prepared by mixing the oil phase into the water phase. The water phase consisted of 73.76% water, 0.5% hydroxyethyl cellulose, 0.5% hydroxypropyl starch phosphate, 4% glycerin, 0.04% disodium EDTA, and preservative and perfume. The oil phase consisted of 6% of soya oil gel of the present invention (20% Vector 4111 and 80% soya oil), 10% sunflower oil, 3% Shea Butter, 1% PJ, 0.2% Polysorbate 20, 0.5% Distearyldimonium Chloride, and perfume and preservative.

Although this invention has been described with a certain degree of particularity, it is to be understood that the present disclosure has been made only by way of illustration and that numerous changes in the details of construction and arrangement of parts may be resorted to without departing from the spirit and the scope of the invention.

I claim:

1. A composition comprising a blend of:
    (A) from 1 to 50 weight percent of at least one block copolymer, wherein the block copolymer has at least one polystyrene segment and at least one unsaturated rubber segment, and the block copolymer has a polystyrene content from 5% to 80%; and
    (B) from 99 to 50 weight percent of a natural oil containing ester or triglyceride chemical structure;
    wherein said blend exhibits no oil bleeding.

2. The composition of claim 1, wherein said block copolymer is a diblock, triblock, radial, or multiblock copolymer or mixtures thereof.

3. The composition of claim 1, wherein said block copolymer is selected from the group consisting of: polystyrene-polyisoprene-polystyrene, polystyrene-polybutadiene-polystyrene, polystyrene-poly(isoprene-butadiene)-polystyrene, polystyrene-poly (butadiene-styrene)-polystyrene, polystyrene-poly (ethylene-propylene-styrene)-polystyrene, polystyrene-polyisoprene, polystyrene-polybutadiene, polystyrene-poly(isoprene-butadiene), polystyrene-poly (butadiene-styrene), polystyrene-poly (ethylene-propylene-styrene) and mixtures thereof.

4. The composition of claim 1 further comprising skin compatible emollients.

5. The composition of claim 1, further comprising a skin compatible solid wax present in an amount from 1 to 60 percent by weight, and the blend of components (A) and (B) is present in an amount of from 99 to 40 percent by weight of the total composition.

6. The composition of claim 5, wherein the skin compatible solid wax is selected from the group consisting of beeswax and beeswax derivatives, hydrogenated vegetable oils and their derivatives, vegetable waxes and their derivatives, sterols and cholesterol fatty acid esters, phospholipids, sphingo lipids, ceramides, glycosphingo lipids, synthetic ester waxes, solid fatty acids and fatty alcohols and their derivatives, stearic acid, behenyl alcohol, glyceryl monostearate, solid synthetic alcohols, microcrystalline waxes, paraffin waxes, ozokerite, polyethylene, silicone waxes, and mixtures thereof.

7. A composition comprising:
    a blend of:
    (A) from 1 to 50 weight percent of at least one block copolymer, wherein the block copolymer has at least one polystyrene segment and at least one unsaturated rubber segment and the block copolymer has a polystyrene content from 5% to 80%; and
    (B) from 99 to 50 weight percent of a natural oil containing ester or triglyceride chemical structure;
    wherein said blend exhibits no oil bleeding at room temperature, and is from 5 to 99 percent by weight of the composition; and
    (C) an air care active, wherein the air care active is from 0.5 to 40 percent by weight of the composition.

8. The composition of claim 7 wherein the blend additionally comprises a skin compatible solid wax present in an amount from 1 to 60 percent by weight, and the blend of components (A) and (B) is present in an amount of from 99 to 40 percent by weight of the total blend.

9. The composition of claim 8, wherein the air care actives is selected from the group consisting of fragrances, essential oils, deodorizers, masking agents, pest repellents, pesticides, etc and mixtures thereof.

10. The composition of claim 7, where in the composition is in the physical form of slurry, emulsion, gel, or powder of solid or gel particles with a particle size ranging from 0.5 to 500 u.

11. A composition comprising:
a blend of:
(A) from 1 to 50 weight percent of at least one block copolymer, wherein the block copolymer has at least one polystyrene segment and at least one unsaturated rubber segment and the block copolymer has a polystyrene content from 5% to 80%; and
(B) from 99 to 50 weight percent of a natural oil containing ester or triglyceride chemical structure;
wherein said blend exhibits no oil bleeding at room temperature, and is from 1 to 99 percent by weight of the composition; and
(C) from 99 to 1 percent by weight of the composition is selected from the group consisting of health and cosmetically acceptable active, benefit agents, functional, inert and auxiliary ingredients, and mixtures thereof.

12. The composition of claim 11 wherein the blend additionally comprises a skin compatible solid wax present in an amount from 1 to 60 percent by weight, and the blend of components (A) and (B) is present in an amount of from 99 to 40 percent by weight of the total blend.

13. The composition of claim 11 wherein the physical form of the composition is a lotion, cream, paste, gel, stick, aerosol, foam, or powder.

14. A composition comprising:
(A) a benefit blend of:
i. from 1 to 50 weight percent of at least one block copolymer, wherein the block copolymer has at least one polystyrene segment and at least one unsaturated rubber segment and the block copolymer has a polystyrene content from 5% to 80%; and
ii. from 99 to 50 weight percent of a natural oil containing ester or triglyceride chemical structure;
wherein said blend exhibits no oil bleeding at room temperature and is from 98 to 1 percent by weight of the composition; and
(B) a cleansing phase in the amount of 2 to 99% by weight of the composition.

15. The composition of claim 14, wherein the benefit blend further comprises a skin compatible emollient or solid wax present in an amount from 1 to 60 percent by weight, and the blend of components (A) and (B) is present in an amount of from 99 to 20 percent by weight of the total blend.

16. The composition of claim 14, wherein cleansing phase comprises surfactants selected from anionic, amphoteric, zwitterionic, nonionic, cationic surfactants and mixtures thereof.

17. The composition of claim 14, wherein the composition is a personal cleansing composition, comprising the said hydrophobic benefit blend dispersed in a cleansing phase as particles of 0.1 u to 500 u in a concentration of 1% to 60% by weight of the total composition.

18. The cleansing phase of claim 14 is a lamellar structured surfactant phase wherein the concentration of skin compatible surfactants is 2 to 50%.

19. The composition of claim 14, wherein the composition is a soap bar or mild syndet bar and the cleansing phase comprises 20% to 90% by weight of surfactants selected from soap, mild lathering surfactants, or mixtures thereof, and 3% to 20% by weight of binder selected from the group of water, liquid water-soluble aliphatic polyol, polyethylene glycol, polypropylene glycol, and mixtures thereof.

20. The composition of claim 1, wherein said blend exhibits clarity sufficient to read black words on white paper through a gel of 1 cm thickness.

21. A method for producing a stable clear natural oil gel comprising:
(a) blending a mixture of from 1 to 50 weight percent of at least one block copolymer, wherein the block copolymer has at least one polystyrene segment and the block copolymer has a polystyrene content from 5% to 80%, and at least one unsaturated rubber segment with from 99 to 50 weight percent of a natural oil, wherein the natural oils have ester or triglyceride chemical structures;
(b) blending said mixture at a temperature of 100 to 250° C. under slow or moderate mixing speed until said mixture become a homogeneous and clear solution;
(c) cooling said mixture down to room temperature resulting in a gel;
wherein said gel exhibits no oil bleeding.

22. The composition of claim 1, wherein the block copolymer has a polystyrene content of from 10% to 50%.

* * * * *